United States Patent

Sleeper (10) Patent No.: US 9,589,730 B2
(45) Date of Patent: Mar. 7, 2017

(54) FEED-THROUGH ASSEMBLY

(75) Inventor: Scott B. Sleeper, Phoenix, AZ (US)

(73) Assignee: Medtronic, Inc., Minneapolis, MN (US)

( * ) Notice: Subject to any disclaimer, the term of this patent is extended or adjusted under 35 U.S.C. 154(b) by 779 days.

(21) Appl. No.: 13/430,223

(22) Filed: Mar. 26, 2012

(65) Prior Publication Data
US 2012/0182679 A1    Jul. 19, 2012

Related U.S. Application Data

(63) Continuation of application No. 11/331,708, filed on Jan. 13, 2006, now Pat. No. 8,145,313.

(51) Int. Cl.
*A61N 1/39* (2006.01)
*H01G 4/35* (2006.01)

(52) U.S. Cl.
CPC ............. *H01G 4/35* (2013.01); *A61N 1/3956* (2013.01)

(58) Field of Classification Search
CPC ................................. H01G 4/35; A61N 1/3956
USPC ........................................ 607/36–37; 361/302
See application file for complete search history.

(56) References Cited

U.S. PATENT DOCUMENTS

| | | |
|---|---|---|
| 4,940,858 A | 7/1990 | Taylor et al. |
| 5,282,841 A | 2/1994 | Szyszkowski |
| 5,620,476 A | 4/1997 | Truex et al. |
| 5,650,759 A | 7/1997 | Hittman et al. |
| 5,855,995 A | 1/1999 | Haq et al. |
| 5,867,361 A | 2/1999 | Wolf et al. |
| 5,870,272 A | 2/1999 | Seifried et al. |
| 6,031,710 A | 2/2000 | Wolf et al. |
| 6,041,496 A | 3/2000 | Haq et al. |
| 6,055,455 A | 4/2000 | O'Phelan et al. |
| 6,146,743 A | 11/2000 | Haq et al. |
| 6,519,333 B1 | 2/2003 | Malik |
| 6,721,602 B2 | 4/2004 | Engmark et al. |
| 6,768,629 B1 | 7/2004 | Allen et al. |
| 7,214,068 B2 | 5/2007 | Kronich et al. |
| 7,317,946 B2 * | 1/2008 | Twetan et al. .................. 607/60 |
| 2005/0007718 A1 * | 1/2005 | Stevenson et al. ........... 361/118 |
| 2007/0167989 A1 | 7/2007 | Sleeper |

\* cited by examiner

*Primary Examiner* — Rex R Holmes
(74) *Attorney, Agent, or Firm* — Carol F. Barry (57) ABSTRACT

A feed-through assembly is presented. The feed-through assembly includes a first end and a second end with a body therebetween. The first end comprises a substantially L-shaped end and a block. The substantially L-shaped end includes a first contact surface. The block includes a second contact surface.

16 Claims, 9 Drawing Sheets

FEED-THROUGH ASSEMBLY

This is a continuation of patent application Ser. No. 11/331,708, filed Jan. 13, 2006, pending, which is incorporated herein by reference.

FIELD OF THE INVENTION

The present invention relates generally to an electronic device and, more particularly, to a feed-through assembly in an electronic device.

BACKGROUND OF THE INVENTION

Numerous devices (e.g., implantable medical devices (IMDs) electrochemical cells, sensors etc.) are hermetically sealed. Hermetically sealed containers prevent liquid from contacting electronic components within a device. To connect with the electronic components, a feed-through assembly is inserted into a portion of the housing.

A typical feed-through assembly consists of a conductive element (e.g., wires etc.), a ferrule, an insulator member (e.g. glass, ceramic etc.), and a seal. The ferrule includes an aperture configured to receive the insulator member. A seal is located between the ferrule and the insulator member. An eyelet, slipped over the conductive element, is seated into the insulator member.

Electronic devices and feed-through assemblies are typically designed so that a perpendicular bonding orientation exists therebetween. A perpendicular bonding orientation is defined by the conductive element (e.g. wire) being perpendicular to a planar portion (e.g. bottom, side wall etc.) of the housing for the electronic device. Perpendicular bonding orientation may not be used with some electronic components. It is therefore desirable to have a feed-through assembly that overcomes this limitation.

BRIEF DESCRIPTION OF THE DRAWINGS

The present invention will become more fully understood from the detailed description and the accompanying drawings, wherein.

DETAILED DESCRIPTION OF THE EMBODIMENTS

The following description of an embodiment is merely exemplary in nature and is in no way intended to limit the invention, its application, or uses. For purposes of clarity, similar reference numbers are used in the drawings to identify similar elements.

The present invention is directed to a feed-through assembly for a sensor associated with an implantable medical device. A feed-through assembly includes a substantially cylindrically shaped body with a first end and a second end. The first end comprises a substantially L-shaped end and a block. The L-shaped end includes a first contact surface. The block, coupled to the L-shaped end, includes a second contact surface. The feed-through assembly is inserted through a portion of the housing or shield such that the first and second contact surfaces are adjacent to first and second conductive elements (e.g. pins, posts, blocks, pads etc.) of an electronic component. In this configuration, multiple orientations are possible via an interconnect between the first and second contact surfaces and the first and second pins, respectively. For example, the conductive element (e.g. wire etc.), defined as the axis of the feed-through assembly, can be horizontally or vertically-oriented relative to a planar portion of the housing, shield, or printed wiring board.

Additionally, multiple conductive elements (e.g. pins, wires, etc.) from an electronic component may be placed adjacent to each other that are bondable by automated methods (e.g. wirebond, laser ribbon welding, laser wire welding, soldered wire, soldered ribbon, laser welded flex circuit, soldered flex circuit, resistance spot welding, tape automated bonding (TAB), etc.). Moreover, the first and second contact surfaces on the feed-through assembly provide mechanically stable platforms for wirebond interconnect or other interconnect methods. Furthermore, an integrated filter capacitor can be included in the feed-through assembly in which capacitance can be varied by selection of insulating material or by varying geometric factors (e.g. area of an interface and/or gap between signal and ground pins).

Figure 1:
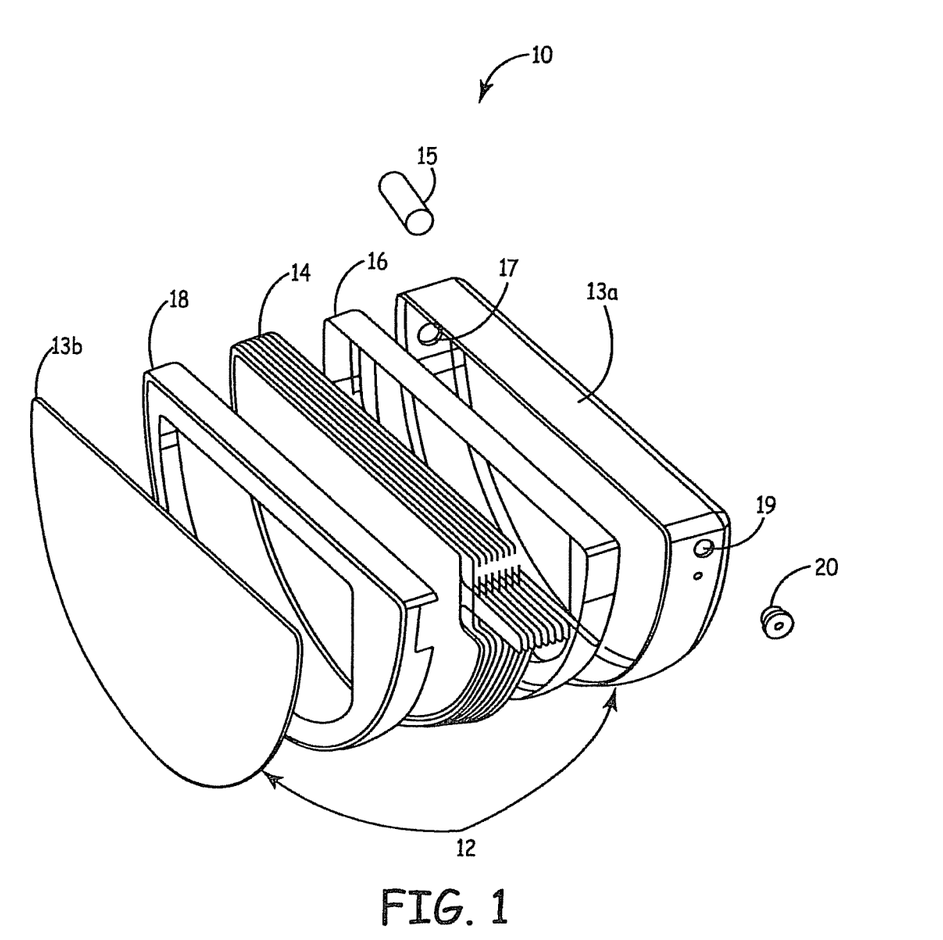
FIG. 1 is a perspective cutaway view of a housing with a feed-through assembly placed therethrough.

Referring now to FIG. 1, an exemplary electronic component such as a capacitor 10 for an implantable medical device (IMD) is depicted. Capacitor 10 includes a housing 12, an electrode stack 14, an inner liner 18, an outer liner 16, a fill port 15 (also referred to as a tube), and a feed-through assembly 20. Housing 12 is formed by a first portion 13a welded to a second portion 13b. Housing 12 also includes apertures 17, 19 in which fill port 15 and feed-through assembly 20 are coupled thereto, respectively. Inner and outer liners 18, 16 surround electrode stack 14 to prevent direct contact between electrode stack 14 and housing 12.

Figure 2:
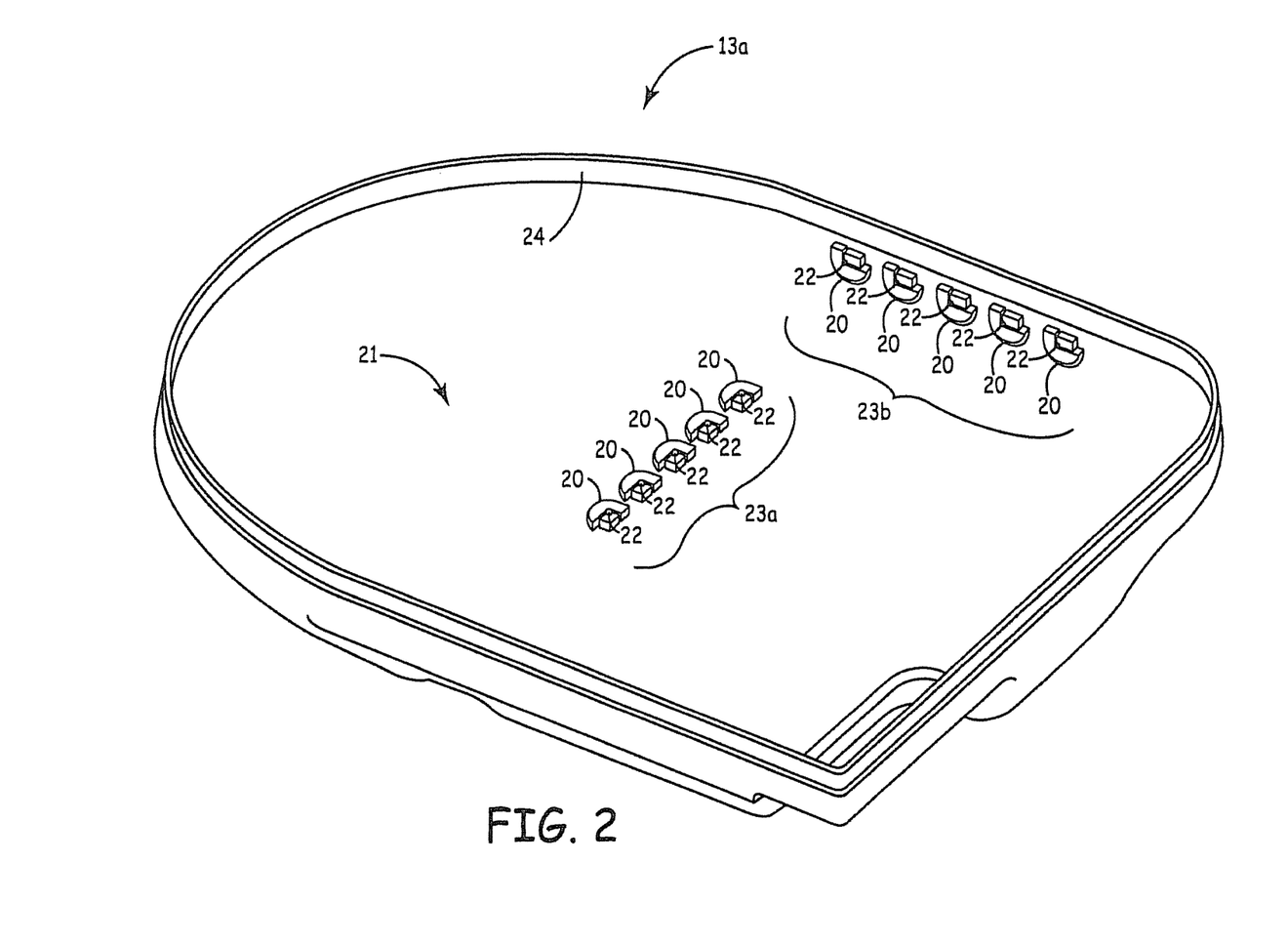
FIG. 2 is a perspective cutaway view of a housing with a plurality of feed-through assemblies placed therethrough.
Figure 3:
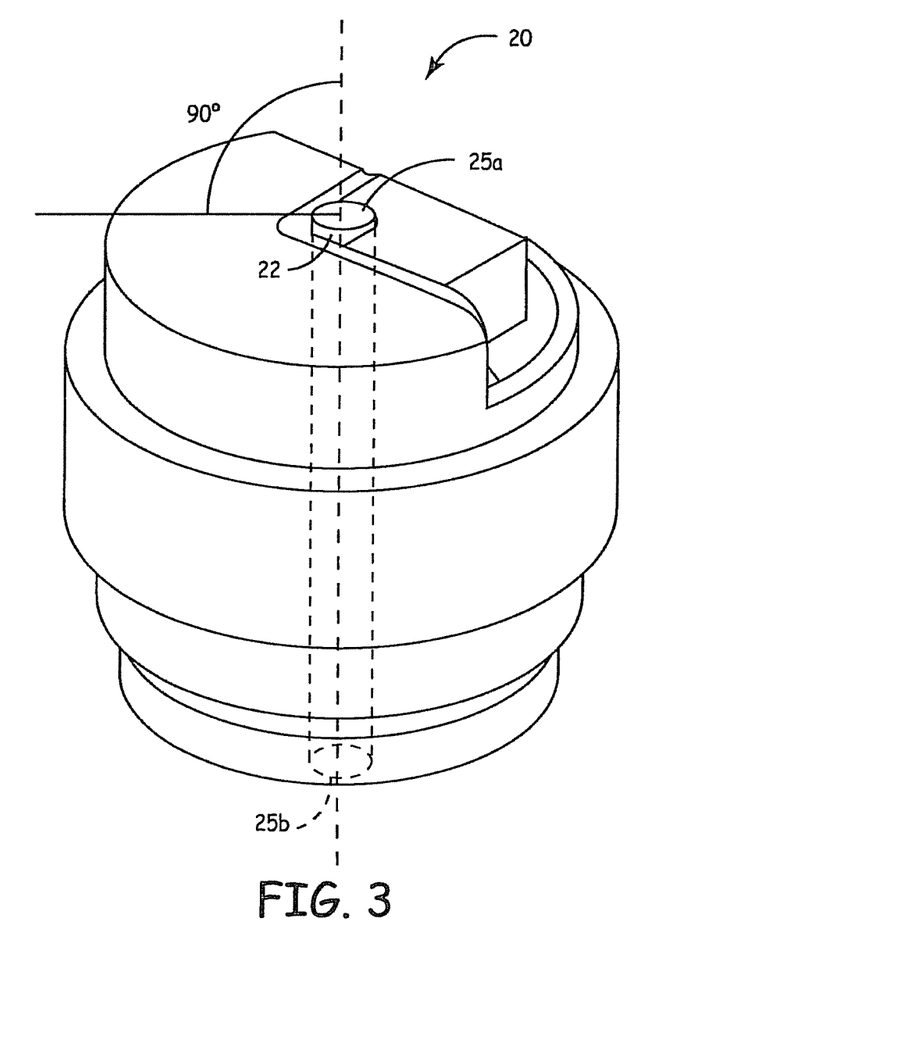
FIG. 3 is a perspective angled view of an exemplary feed-through assembly oriented in a vertical position.
Figure 4:
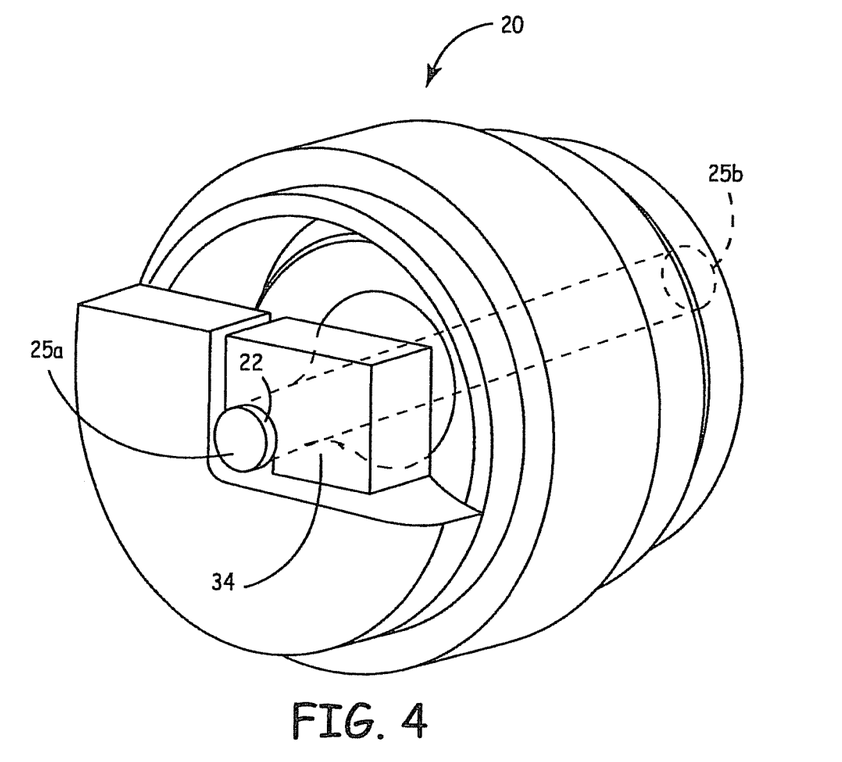
FIG. 4 is a perspective angled view of an exemplary feed-through assembly oriented in a horizontal position.

FIG. 2 depicts first portion 13a of housing 12. First portion 13a includes a bottom 21 and a circumferential side 24. A first and a second set of feed-through assemblies 23a, 23b are inserted through bottom 21 and side 24, respectively. First set of feed-through assemblies 23a in bottom 21 are oriented in a vertical direction, as shown in FIGS. 2 and 3. The vertical orientation is defined by an axis formed by first and second ends 25a, 25b of conductive element 22 (e.g. wire, etc.) oriented perpendicular to bottom 21. In contrast, feed-through assembly 23b is oriented in a horizontal direction along side 24 by first and second ends 25a, 25b being parallel to bottom 21, as shown in FIGS. 2 and 4.

Figure 5:
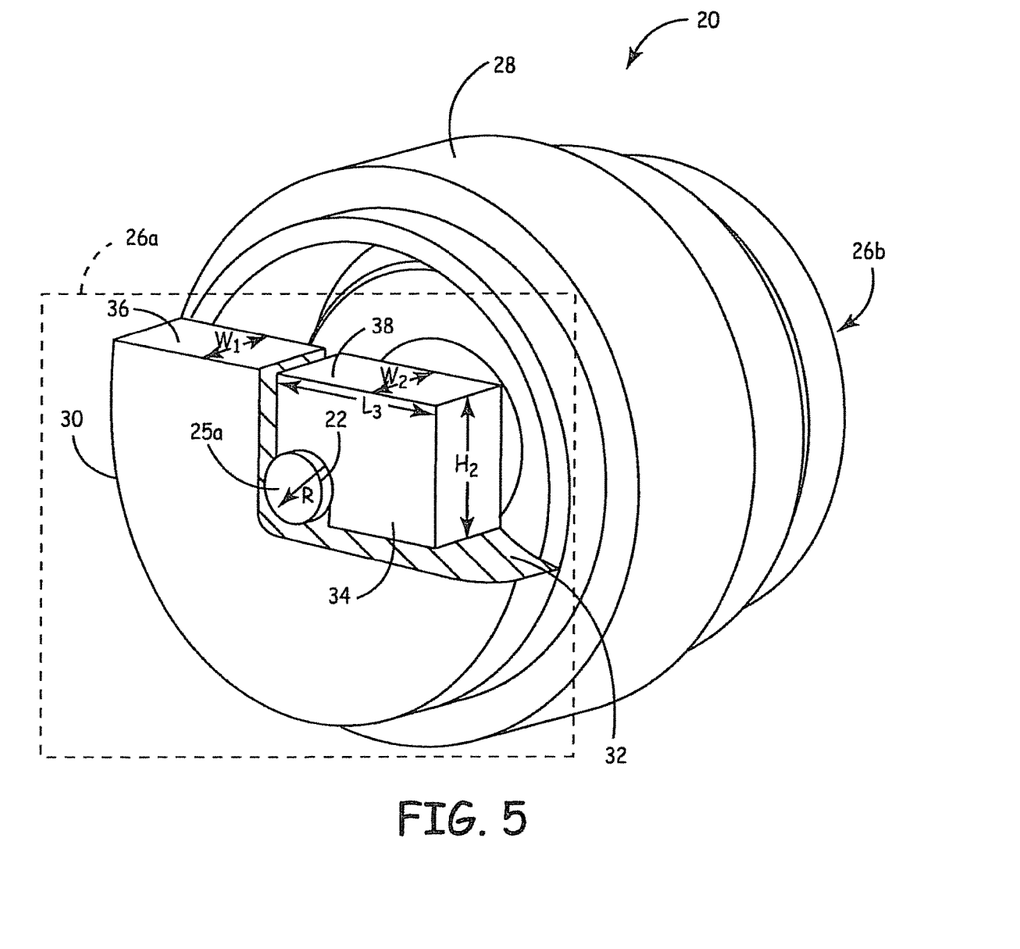
FIG. 5 is an angled perspective view of a first end of an exemplary feed-through assembly.
Figure 6:
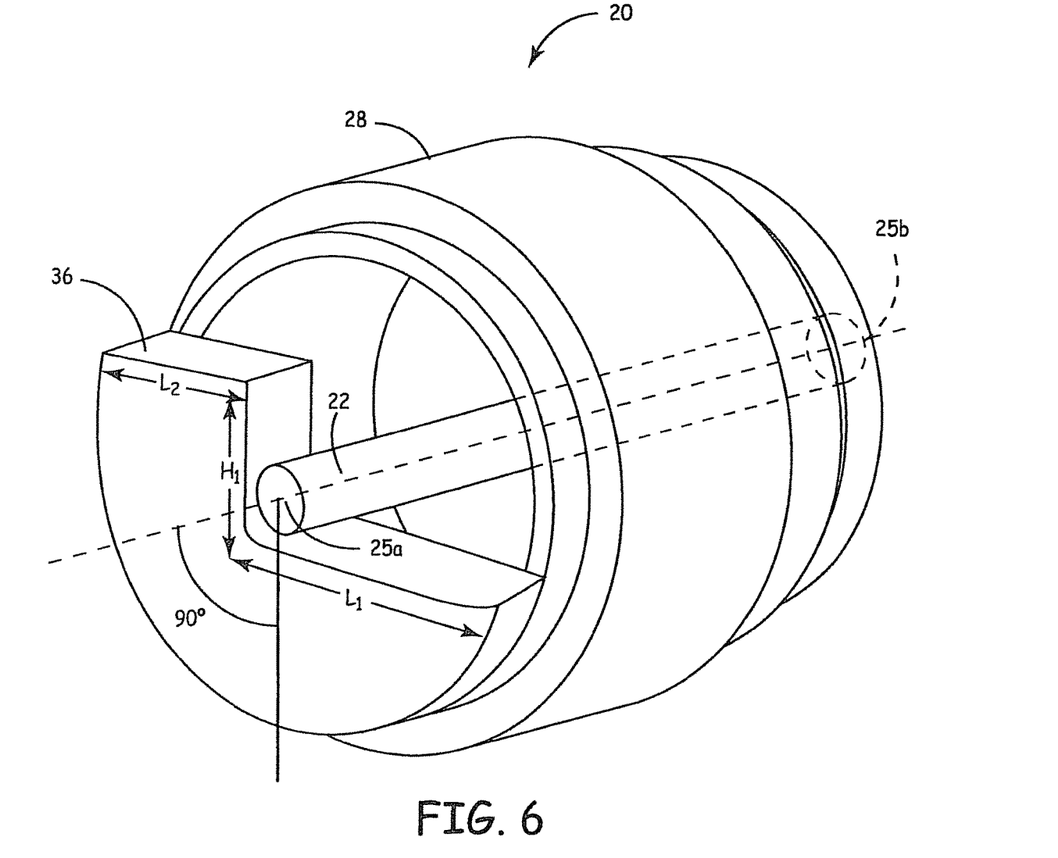
FIG. 6 is an angled perspective view of a portion of a first end of an exemplary feed-through assembly without insulating material and a block.

FIGS. 5 and 6 depict details of feed-through assembly 20 that allow different orientations (i.e. vertical orientation and horizontal orientation) to occur between feed-through assembly 20 and first portion 13a. Feed-through assembly 20 includes a first end 26a (ghost lines) and a second end 26b with a substantially cylindrically shaped body 28 therebetween. Body 28 has a diameter of about 0.130 inches and is comprised of a metallic material.

First end 26a comprises a substantially L-shaped end 30, conductive element 22, insulating material 32, and block 34. Substantially L-shaped end 30 includes a first length (L1), a second length (L2), a height (H1), and a first contact surface 36. L1 ranges from about 0.035 to about 0.069 inches; L2 ranges from about 0.015 to about 0.037 inches; and H1 ranges from about 0.015 to about 0.037 inches. The width (W1) of first contact surface 36 ranges from about 0.015 to about 0.023 inches.

Insulating material 32 is disposed between L-shaped end 30 and block 34. Insulating material 32 may comprise epoxy and hardener, polyimide, ceramic with an adhesive film or other suitable material.

Block 34, coupled to the substantially L-shaped first end 30, includes a second contact surface 38. Block 34 is defined by length (L3), height (H2) and radial aperture portion R. L3 ranges from about 0.015 inches to about 0.047 inches and H2 ranges from about 0.020 inches to about 0.033 inches. Radial aperture portion is configured to receive conductive element 22. R ranges from about 0.006 to about 0.009 inches. The width (W2) of second contact surface 38 ranges from about 0.015 to about 0.023 inches. Skilled artisans appreciate that these dimensions may be increased or decreased depending upon the size of feed-thorough assembly 20.

Figure 7:
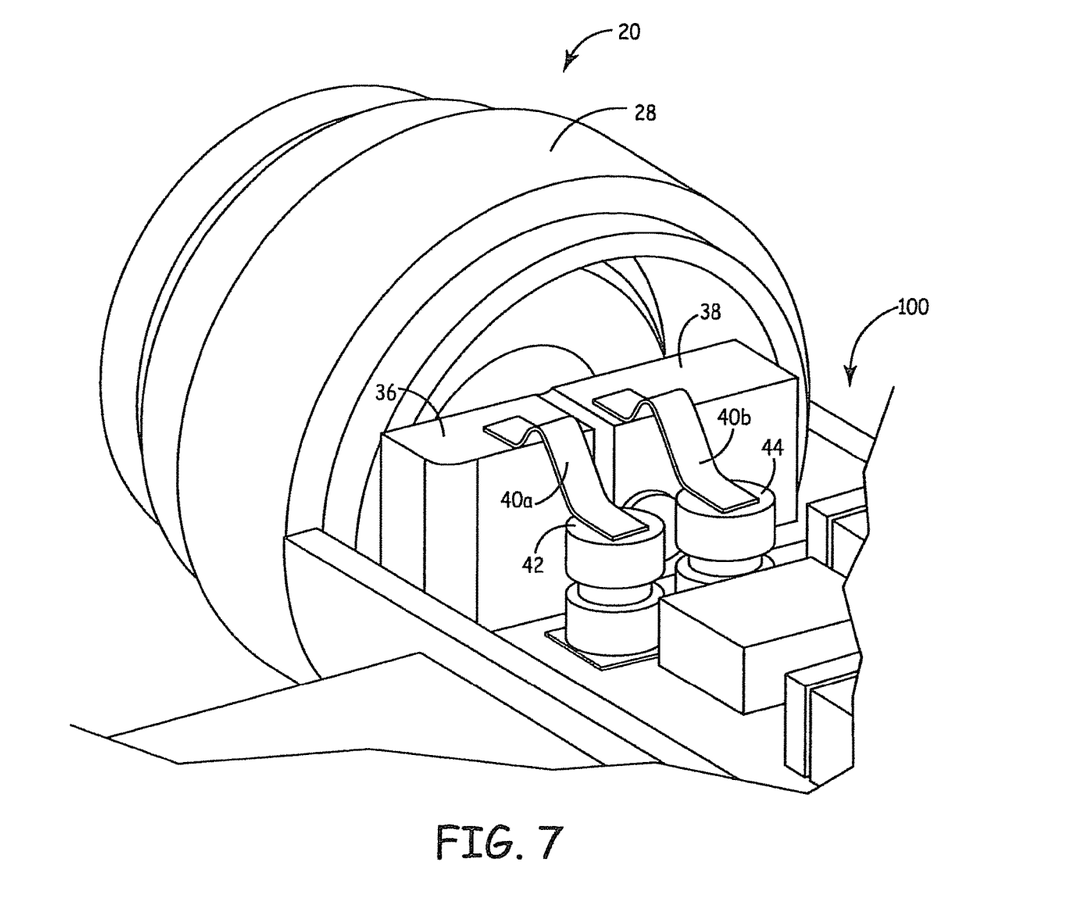
FIG. 7 is an angled perspective view of an exemplary feed-through assembly coupled to an electronic component.

FIG. 7 depicts feed-through assembly 20 mounted in a horizontal orientation to a housing 100. In this embodiment, housing 100 relates to a different electronic component such as a sensor used in conjunction with implantable medical devices. An example of such a sensor may be seen with respect to U.S. patent application Ser. No. 10/733,000, and assigned to the assignee of the present invention, the disclosure of which is incorporated by reference in relevant parts.

Housing 100 includes first and second pins 42 and 44, respectively. First pin 42 is a ground pin and second pin 44 is a center pin or signal pin. First pin 42 is coupled to first contact surface 36 via interconnect 40a while second pin is coupled to second contact surface 38 via interconnect 40b. Interconnect 40a, 40b may be formed by wirebonding, laser ribbon welding, laser wire welding, soldered wire, soldered ribbon, laser welded flex circuit, soldered flex circuit, resistance spot welding, or TAB bonding. Interconnect 40a, 40b comprise conductive material such as nickel clad copper, aluminum, gold, copper, nickel, tungsten, tantalum, titanium, or other suitable material.

Figure 8:
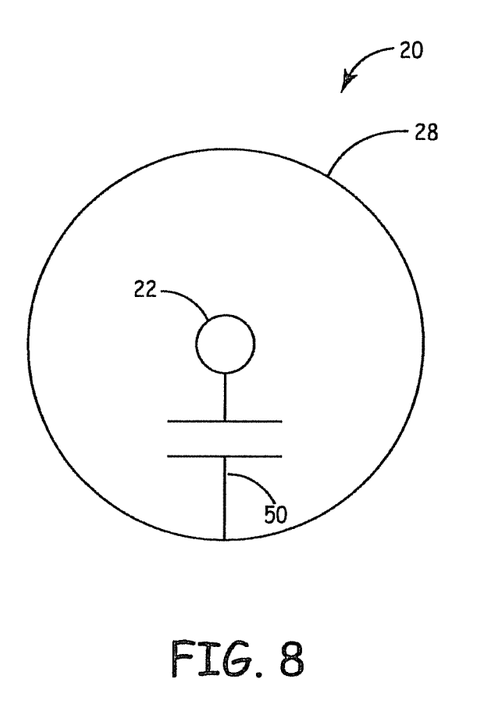
FIG. 8 is a top perspective view a feed-through assembly that includes a capacitor.

FIG. 8 depicts another embodiment of a filtered feed-through assembly 20 that includes a capacitor 50. Capacitance on capacitor 50 may be modified to meet requirements specified by electronic components.

Figure 9:
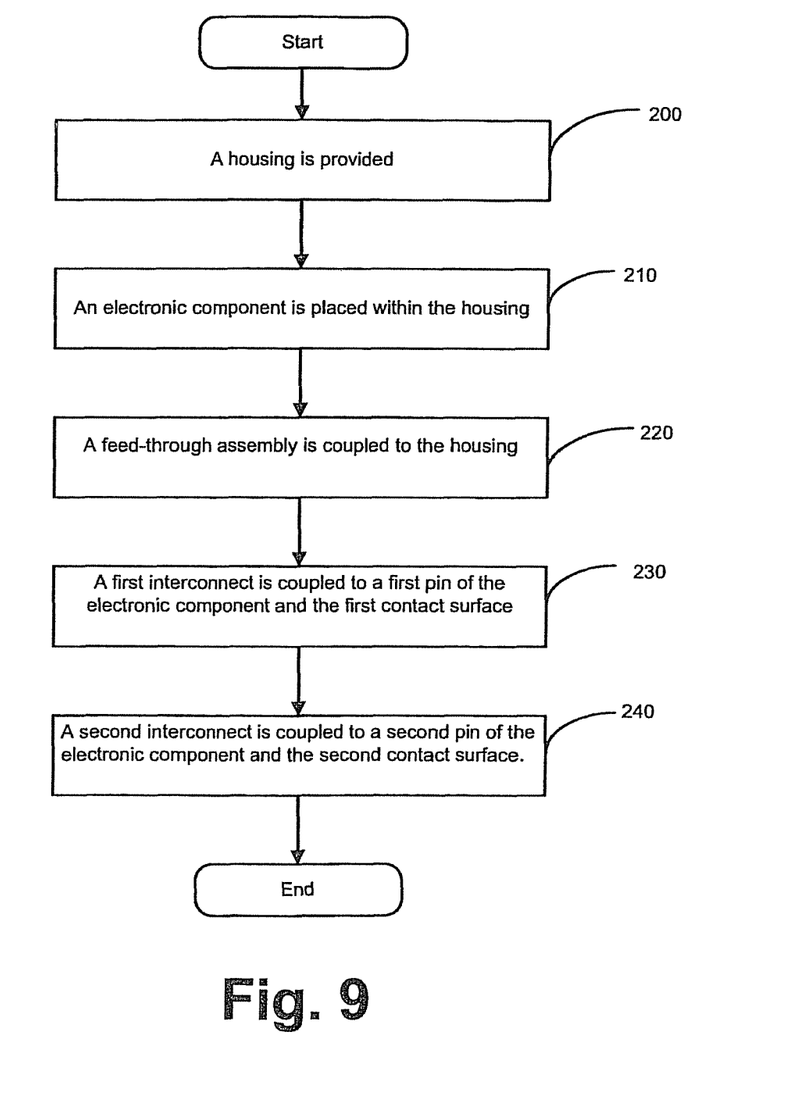
FIG. 9 is flow diagram for connecting a feed-through assembly with an electronic component.

FIG. 9 is a flow diagram that depicts formation of an IMD that includes feed-through assembly 20. At operation 200, a housing is provided. An electronic component is placed within the housing at operation 210. A feed-through assembly is coupled to the housing at operation 220. The feed-through assembly includes a first end and a second end with a body therebetween. The first end includes a first contact surface and a second contact surface. At operation 230, a first interconnect is coupled to a first pin of the electronic component and the first contact surface of the feed-through assembly. At operation 240, a second interconnect is coupled to a second pin of the electronic component and the second contact surface of the feed-through assembly.

The present invention has numerous applications. For example, while the figures relate to unipolar feed-through assemblies, other types of feed-through assemblies (quadripolar feed-through assemblies etc.) may also rely on this process to reliably produce quality feed-through assemblies. Skilled artisans also appreciate that while feed-through assembly 20 is used relative to sensor housing 100, feed-through assembly may be used in a variety of other electronic components (e.g. commercial or military electronic packaging, optoelectronic packaging, telecommunications etc). Additionally, while the first and second contact surfaces are depicted as flat surfaces, first and second contact surfaces may also have substantially rounded edges. The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. An implantable medical device comprising:
    a housing comprising a bottom wall and a side wall;
    an electronic component disposed within the housing and having first and second conductors;
    a first feed-through assembly inserted through the bottom wall of the housing and a second feed-through assembly inserted through the side wall of the housing, wherein each of the feed-through assemblies includes:
        a body having a first end positioned inside the housing and a second end positioned outside the housing,
        a conductive element carried within and extending through the body, wherein a first end of the elongated conductive element is located inside the housing and the second end of the elongated conductive element is located outside of the housing, and wherein the conductive element defines an axis extending between the first end and the second end of the conductive element,
        a first conductive block located inside the housing proximate the first end of the body, the first conductive block comprising a first contact surface located within the housing, wherein the first contact surface comprises a flat surface,
        a second conductive block located inside the housing proximate the first end of the body, the second conductive block comprising a second contact surface located within the housing, wherein the second contact surface comprises a flat surface,
        insulating material disposed between the first conductive block and the second conductive block, wherein a portion of the conductive element is positioned between the first conductive block and the second conductive block, and wherein the insulating material electrically insulates the first conductive block from the conductive element;
    wherein the first contact surface and the second contact surface of the first feed-through are oriented vertically when the bottom wall of the housing is oriented horizontally;
    wherein rotation of the second feed-through about the axis defined by the conductive element rotates the orientation of the first contact surface and the second contact surface relative to the bottom wall;
    wherein, for each of the first and second feed-through assemblies, the second conductive block comprises a radial aperture portion facing the first conductive block wherein the elongated conductive element is located between the first conductive block and in direct contact with the radial aperture portion of the second conductive block;
    and wherein the radial aperture portion of the second conductive block does not completely surround the elongated conductive element located between the first conductive block and the radial aperture portion of the second conductive block.

2. The implantable medical device of claim 1, wherein the first contact surface and the second contact surface of the second feed-through are oriented horizontally when the bottom wall of the housing is oriented horizontally.

3. The implantable medical device of claim 1, wherein, for each of the first and second feed-through assemblies, the first conductive block comprises a substantially L-shaped body and the second conductive block is nested within the substantially L-shaped body of the first conductive block.

4. The implantable medical device of claim 1, wherein, for each of the first and second feed-through assemblies, the first contact surface and the second contact surface face in the same direction.

5. The implantable medical device of claim 1, wherein, for each of the first and second feed-through assemblies, the first contact surface and the second contact surface face in the same direction and are located next to each other.

6. The implantable medical device of claim 1, wherein, for each of the first and second feed-through assemblies, the insulating material is in direct contact with the first conductive block and the conductive element.

7. The implantable medical device of claim 1, wherein the first conductive block of the first feed-through assembly is electrically connected to the first conductor of the electronic component by a first interconnect extending between the first contact surface and the first conductor;
and wherein the second conductive block of the first feed-through assembly is electrically connected to the second conductor of the electronic component by a second interconnect extending between the second contact surface and the second conductor.

8. The implantable medical device of claim 1, wherein the first conductive block of the second feed-through assembly is electrically connected to the first conductor of the electronic component by a first interconnect extending between the first contact surface and the first conductor;
and wherein the second conductive block of the second feed-through assembly is electrically connected to the second conductor of the electronic component by a second interconnect extending between the second contact surface and the second conductor.

9. An implantable medical device comprising:
a housing comprising a bottom wall and a side wall;
an electronic component disposed within the housing and having first and second conductors;
a first feed-through assembly inserted through the bottom wall of the housing and a second feed-through assembly inserted through the side wall of the housing, wherein each of the feed-through assemblies includes:
a body having a first end positioned inside the housing and a second end positioned outside the housing,
a conductive element carried within and extending through the body, wherein a first end of the elongated conductive element is located inside the housing and the second end of the elongated conductive element is located outside of the housing, and wherein the conductive element defines an axis extending between the first end and the second end of the conductive element,
a first conductive block located inside the housing proximate the first end of the body, the first conductive block comprising a first contact surface located within the housing, wherein the first contact surface comprises a flat surface, and wherein the first conductive block comprises a substantially L-shaped body,
a second conductive block located inside the housing proximate the first end of the body, the second conductive block comprising a second contact surface located within the housing, wherein the second contact surface comprises a flat surface and wherein the second conductive block is nested within the substantially L-shaped body of the first conductive block,
insulating material disposed between the first conductive block and the second conductive block, wherein a portion of the conductive element is positioned between the first conductive block and the second conductive block, and wherein the insulating material electrically insulates the first conductive block from the conductive element and is in direct contact with the first conductive block and the conductive element;
wherein the first contact surface and the second contact surface of the first feed-through are oriented vertically when the bottom wall of the housing oriented horizontally;
wherein rotation of the second feed-through about the axis defined by the conductive element rotates the orientation of the first contact surface and the second contact surface relative to the bottom wall;
wherein, for each of the first and second feed-through assemblies, the first contact surface and the second contact surface face in the same direction;
wherein, for each of the first and second feed-through assemblies, the second conductive block comprises a radial aperture portion facing the first conductive block, wherein the elongated conductive element is located between the first conductive block and in direct contact with the radial aperture portion of the second conductive block;
and wherein the radial aperture portion of the second conductive block does not completely surround the elongated conductive element located between the first conductive block and the radial aperture portion of the second conductive block.

10. The implantable medical device of claim 9, wherein the first contact surface and the second contact surface of the second feed-through are oriented horizontally when the bottom wall of the housing is oriented horizontally.

11. The implantable medical device of claim 9, wherein, for each of the first and second feed-through assemblies, the first contact surface and the second contact surface are located next to each other.

12. The implantable medical device of claim 9, wherein the first conductive block of the first feed-through assembly is electrically connected to the first conductor of the electronic component by a first interconnect extending between the first contact surface and the first conductor;
and wherein the second conductive block of the first feed-through assembly is electrically connected to the second conductor of the electronic component by a second interconnect extending between the second contact surface and the second conductor.

13. The implantable medical device of claim 9, wherein the first conductive block of the second feed-through assembly is electrically connected to the first conductor of the electronic component by a first interconnect extending between the first contact surface and the first conductor;

and wherein the second conductive block of the second feed-through assembly is electrically connected to the second conductor of the electronic component by a second interconnect extending between the second contact surface and the second conductor.

14. An implantable medical device comprising:
a housing comprising a bottom wall and a side wall;
an electronic component disposed within the housing and having first and second conductive elements;
a first feed-through assembly inserted through the bottom wall of the housing and a second feed-through assembly inserted through the side wall of the housing, wherein each of the feed-through assemblies includes:
   a body having a first end positioned inside the housing and a second end positioned outside the housing,
   a conductive element carried within and extending through the body, wherein a first end of the elongated conductive element is located inside the housing and the second end of the elongated conductive element is located outside of the housing, and wherein the conductive element defines an axis extending between the first end and the second end of the conductive element,
   a first conductive block located inside the housing proximate the first end of the body, the first conductive block comprising a first contact surface located within the housing, wherein the first contact surface comprises a flat surface, and wherein the first conductive block comprises a substantially L-shaped body,
   a second conductive block located inside the housing proximate the first end of the body, the second conductive block comprising a second contact surface located within the housing, wherein the second contact surface comprises a flat surface, and wherein the second conductive block is nested within the substantially L-shaped body of the first conductive block, and further wherein the second conductive block comprises a radial aperture portion facing the first conductive block, wherein the elongated conductive element is located between the first conductive block and in direct contact with the radial aperture portion of the second conductive block, and still further wherein the radial aperture portion of the second conductive block does not completely surround the elongated conductive element located between the first conductive block and the radial aperture portion of the second conductive block,
   insulating material disposed between the first conductive block and the second conductive block, wherein a portion of the conductive element is positioned between the first conductive block and the second conductive block, and wherein the insulating material electrically insulates the first conductive block from the conductive element and is in direct contact with the first conductive block and the conductive element;
wherein the first contact surface and the second contact surface of the first feed-through are oriented vertically when the bottom wall of the housing is oriented horizontally;
wherein rotation of the second feed-through about the axis defined by the conductive element rotates the orientation of the first contact surface and the second contact surface relative to the bottom wall;
wherein, for each of the first and second feed-through assemblies, the first contact surface and the second contact surface face in the same direction and are located next to each other.

15. The implantable medical device of claim 14, wherein the first contact surface and the second contact surface of the second feed-through are oriented horizontally when the bottom wall of the housing is oriented horizontally.

16. The implantable medical device of claim 14, wherein, for each of the first and second feed-through assemblies, the insulating material is in direct contact with the first conductive block and the conductive element.

* * * * *